United States Patent [19]

Thuillier et al.

[11] 4,179,516
[45] Dec. 18, 1979

[54] ETHERS OF 3,4-DIHYDRO-1-BENZOXEPIN-5-ONE OXIME TO TREAT INTESTINAL DISORDERS

[75] Inventors: Germaine Thuillier, Paris; Jacqueline Laforest, Vincennes; Pierre Bessin, Chilly-Mazarin, all of France

[73] Assignee: Albert Rolland, S.A., Paris, France

[21] Appl. No.: 877,616

[22] Filed: Feb. 14, 1978

Related U.S. Application Data

[60] Division of Ser. No. 685,410, May 11, 1976, abandoned, which is a continuation of Ser. No. 492,911, Jul. 29, 1974, abandoned.

[30] Foreign Application Priority Data

Jul. 31, 1973 [FR] France .................. 73 28038
May 22, 1974 [FR] France .................. 74 17976

[51] Int. Cl.$^2$ ............... A61K 27/00; A61K 31/40; A61K 31/335
[52] U.S. Cl. .................. 424/278; 260/333; 424/248.57; 424/274
[58] Field of Search .......... 424/278, 248.57, 274; 260/333

[56] References Cited

U.S. PATENT DOCUMENTS

| 3,793,345 | 2/1974 | Yale et al. ............ 260/333 |
| 3,813,396 | 5/1974 | Yale et al. ............ 260/333 |

FOREIGN PATENT DOCUMENTS

| 1018995 | 2/1966 | United Kingdom ............ 260/333 |
| 1119329 | 7/1968 | United Kingdom ............ 260/333 |
| 1128734 | 10/1968 | United Kingdom ............ 260/333 |

OTHER PUBLICATIONS

M. Protiva et al., Collection Czechosolov. Chem. Commun., vol. 37, (1972), pp. 868-886.

Primary Examiner—Stanley J. Friedman

[57] ABSTRACT

Therapeutic compositions, particularly for treating intestinal disorders, and a method of treating colopathics by administering an effective amount of the compositions are described. The compositions contain a therapeutically effective amount of at least one isomer of the oximino group of the compound having the formula:

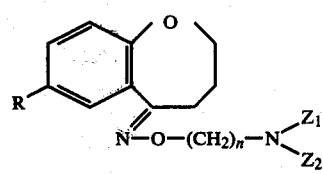

in which:
R is selected from the group consisting of halogen atoms and lower alkoxy groups;
n is an integer 2 or 3, and
$Z_1$ and $Z_2$ are the same or different lower alkyl groups, or
$NZ_1Z_2$ represents a saturated heterocyclic group which may have a second heteroatom selected from the group consisting of N and O,
and the addition salts of the amino group with pharmaceutically acceptable acids,
with a physiological acceptable excipient.

3 Claims, No Drawings

ETHERS OF 3,4-DIHYDRO-1-BENZOXEPIN-5-ONE OXIME TO TREAT INTESTINAL DISORDERS

This is a division of application Ser. No. 685,410, filed May 11, 1976, which is a continuation of Ser. No. 492,911 filed July 29, 1974 both are abandoned.

This invention relates to basic ethers of 3,4-dihydro-1-benzoxepin-5-one oxime, the acid addition salts of the free amines a process for preparing these products, and their therapeutic application.

An ether of 3,4-dihydro-1-benzoxepin-5-one oxime has already been described in Collection Czechoslov. Chem. Common 37 868-886 (1972). It has the following formula:

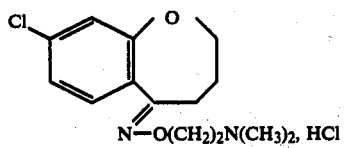

$N-O(CH_2)_2N(CH_3)_2$, HCl

It differs from the compounds with which this invention is concerned by the position of the substituent of the benzene nucleus and, according to the authors of the article, it was found when subjected to pharmacological tests to have only a weak spasmolytic action which could not be utilised.

The basic ethers of 3,4-dihydro-1-benzoxepin-5-one oxime of this invention correspond to the following general formula (I):

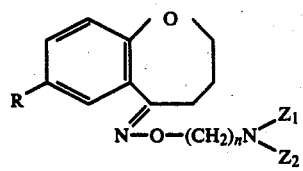

$N-O-(CH_2)_nN\genfrac{}{}{0pt}{}{Z_1}{Z_2}$ (I)

in which:
R represents a halogen atom or a lower alkoxy group;
n is an integer which has the value 2 or 3;
$Z_1$ and $Z_2$, which are identical or different, each represent a lower alkyl group, or $Z_1$ and $Z_2$ and the nitrogen atom to which they are attached together represent a 5-membered to 7-membered N-heterocyclic ring which may include a second hetero atom, in particular N, O or S, in the ring.

Formula (I) represents the two geometric isomers of the oxime, in the cis or trans configuration relative to the benzene nucleus.

The oxime ethers (I) just defined in this way have in particular a relaxant activity at the level of the smooth intestinal muscle fibres which is believed to be of a novel type and they may be used in human therapeutics, in particular as intestinal regulators.

In particular, we provide novel therapuetic compositions which contain, in combination with a physiologically acceptable excipient, at least one compound of formula (I) and/or one of its pharmaceutically acceptable acid addition salts.

The products of the invention may be administered orally in the form of pills and tablets, rectally or parenterally, the daily dose being between 50 and 500 mg, and the unit doses being at least 25 mg.

According to our invention; we provide a process for the preparation of a compound of formula (I) as defined above in which intramolecular acylation is carried out on a phenoxybutyric acid which has a substituent R in the para position to yield a 3,4-dihydro-1-benzoxepin-5-one of the formula (II):

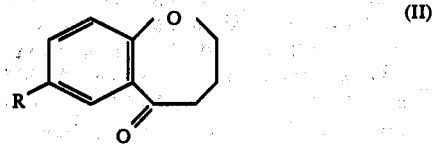

wherein R is as defined above; in which the product of formula (II) is then reacted with a compound of the formula (III)

$H_2N-O-A$ (III)

in which A represents either a hydrogen atom or the group $(CH_2)_n-NZ_1Z_2$ where n, $Z_1$ and $Z_2$ are defined as above, provided that, when A is $(CH_2)_n-NZ_1Z_2$, the reaction is carried out in an alcoholic solvent in an acid medium and at the reflux temperature of the solvent, and when A is H, the reaction is carried out in pyridine or ethanol under reflux; and in which the intermediate compound thereby obtained is then reacted in the presence of a base with a compound of the formula (IV):

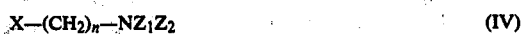

$X-(CH_2)_n-NZ_1Z_2$ (IV)

in which: X is a halogen atom and n, $Z_1$ and $Z_2$ are as defined above.

The acid addition salts of compounds of formula (I) are prepared by the action of a mineral or organic acid on the amine in a suitable solvent.

We have found that the products prepared in this way consist to an extent of 95 to 100% of the geometric isomer of the oxime which has the cis configuration in relation to the benzene nucleus (determined with the aid of nuclear magnetic resonance, infrared spectography and gas phase chromatography). Isolation of this isomer is achieved with excellent yields by successive recrystallisations of mixture of addition salts of the free amine with suitably chosen acids.

Isolation of the trans homologue, on the other hand, cannot be achieved satisfactorily. Partial isomerisation may be carried out by a known method after the introduction of the oxyimino function on to the heterocyclic group, that is to say by the action of a strong anhydrous acid, preferably an anhydrous hydrohalic acid, in an aprotonic solvent.

If this operation is carried out on a compound of the following formula (V):

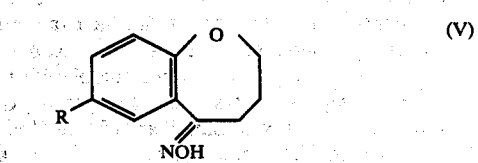

substitution is subsequently carried out on the oxygen atom by the usual method. Separation is achieved as in the case of the cis homologue by the recrystallisation of the acid addition salt, taking into account the fact that the trans isomer is generally more soluble than the cis homologue.

Other advantages and characteristics of the invention will be better understood by reference to the examples of preparation given below, which are in no way limiting but are given purely by way of illustration.

The melting points indicated were determined on a Kofler bench. Elementary analysis of the novel compounds was carried out and the results corresponded to the generally accepted norms (element determined: C, H, N, halogen). The electronic paramagnetic resonance value confirmed that substitution was on the oxygen atom and not on the nitrogen atom of the oxime.

EXAMPLE 1

7-chloro-3,4-dihydro-1-benzoxepin-O-(dimethylamino ethyl)-5-one oxime

A—7-chloro-3,4-dihydro-1-benzoxepin-5-one 30 ml of 85% phosphoric acid (d=1.71) are poured into 530 ml of anhydrous toluene, and 84 g of anhydrous phosphoric acid are then added slowly with vigorous stirring. The mixture is kept on a boiling water bath for 2 hours, and a tepid solution of 24 g of p-chlorophenoxybutyric acid (Mp.=123° C). in 800 ml of anhydrous toluene is then added in the course of 2 hours, always at that temperature. The reaction mixture is heated for a further 5 hours and then cooled.

The upper toluene phase is separated, shaken in the presence of an equal volume of water and then after decantation shaken twice with the same volume of 5% soda. It is then neutralised by washing with water and dried over sodium sulphate. After evaporation of the solvent under reduced pressure, 11.5 g of a yellow oil are obtained.

The lower, phosphoric phase is poured over 3 volumes of crushed ice. This solution is extracted twice with ether at room temperature.

The ethereal phases are shaken in the presence of 5% soda and after decantation of the aqueous phase they are neutralised and dried over sodium sulphate. After evaporation of the solvent under reduced pressure, 5 g of yellow oil are obtained.

The two oily fractions are combined and distilled under reduced pressure. 12 g of ketone are obtained in the form of a colourless liquid with a boiling point of 105°–108° C. at 0.02 mm.Hg.

B—7-chloro-3,4-dihydro-1-benzoxepin-5-one oxime

A solution of 50 g of the benzoxepine previously obtained and 26 g of hydroxylamine hydrochloride in 200 ml of pyridine is kept at the reflux temperature of pyridine for 5½ hours.

The pyridine is then evaporated under reduced pressure. 300 ml of water are poured over the evaporation residue and the aqueous phase is extracted three times with ether. The organic solutions are washed with water until the wash waters are neutral and dried over sodium sulphate and then over magnesium sulphate and the solvent is then evaporated under reduced pressure.

The evaporation residue is recrystallised in absolute ethanol. 47 g of pure oxime are obtained in the form of a white product which melts at 101°–102° C.

C—7-chloro-3,4-dihydro-1-benzoxepin-O-(dimethylaminoethyl)-5-one oxime 7.1 g of the oxime previously obtained are introduced into 30 ml of a solution of sodium ethylate in ethanol (prepared from 0.9 g of sodium). The reaction mixture is heated at the reflux temperature of the solvent for a period of 1 hour. 50 ml of anhydrous dimethylformamide are then introduced and the ethanol is evaporated under reduced pressure. 4 g of (2-chloro)-ethyldimethylamine are added and the mixture is kept at 80° C. for 6 hours. It is then cooled, the mineral salts are filtered and the solvent is evaporated under reduced pressure.

The residue is dissolved in an aqueous solution of normal hydrochloric acid, and after extraction with ether the solution is make alkaline by the addition of a normal soda solution. The oxime ether is then extracted with methylene chloride, and after drying the solvent is evaporated.

The oily residue is dissolved in ether from which the hydrochloride of the amine is then precipitated by the addition of hydrochloric acid. The hydrochloride is recrystallised from a mixture of ethyl acetate and isopropanol (75:25). It melts at 180° C. The yield of this stage is 40%.

EXAMPLE 2

7-chloro-3,4-dihydro-1-benzoxepin-O-(diethylaminoethyl)-5-one oxime: isomer with the cis configuration in relation to the benzene nucleus.

1.2 g of 50% sodium hydride are added slowly with stirring and slight cooling to a solution of 5 g of 7-chloro-3,4-dihydro-1-benzoxepin-5-one oxime in 25 ml of anhydrous dimethylformamide. This sodium salt may also be prepared by the reaction of sodium ethylate in ethanol followed by dissolving in dimethylformamide.

After 1 hour's stirring at room temperature, 3.1 g of (2-chloro)-ethyl diethylamine are introduced into the reaction mixture in the course of 15 minutes. One hour later, 200 ml of water are added and the end product is extracted with ether. It is then extracted from the ether with a 5% acetic acid solution. The aqueous phase is then made alkaline by the addition of $K_2CO_3$ and the amine is again extracted with ether.

After drying of the organic solution, the solvent is evaporated and the oil which remains behind is distilled under reduced pressure.

The boiling point of the basic oxime ether obtained as an end product is 137° C. at $2 \times 10^{-2}$ mm.Hg. The yield of distilled amine is 60%.

The hydrochloride prepared in ether is recrystallised from a mixture of isopropyl ether and 1,2-dichloroethane (60:40). It melts at 115°–116° C.

This salt can also be recrystallised from ethyl acetate but if it is subjected to prolonged heating in the course of this operation another crystalline form of the product appears, which has a melting point of 132° C.

The geometric isomer of this oxime ether which has the cis configuration in relation to the benzene nucleus may advantageously be separated from traces of its trans homologue in the form of its addition salt with hydrobromic acid by recrystallisation from isopropanol. This hydrobromide melts at 114° C.

EXAMPLE 3

7-chloro-3,4-dihydro-1-benzoxepin-O-(diethylaminoethyl)-5-one oxime: trans isomer A solution of 50 g of 7-chloro-3,4-dihydro-1-benzoxepin-5-one oxime in 800 cc of anhydrous chloroform is saturated with anhydrous hydrochloric acid and this mixture is kept at a temperature of 20° C. for about 24 hours with stirring. The precipitate formed is then isolated and the filtrate is twice brought into contact with an aqueous saturated sodium bicarbonate solution and then with water until neutral. The organic phase is dehydrated with sodium sulphate and the solvent is then evaporated under reduced pressure. The evaporation residue is recrystallised from cyclohexane. 40 g of product melting in the region of 95° C. are obtained. It consists of a mixture of nearly equivalent proportions of the two geometric isomers of the oxime.

The geometric isomer which has the trans configuration in relation to the benzene nucleus can be separated from its homologue by chromatography of this mixture on a silica column, using diethyl ether as the eluent. It melts at 150° C. after recrystallisation from isopropanol.

O-alkylation of a 50/50 mixture of the two isomers is carried out in dimethylformamide, applying the method, described in example 2. The crude amine obtained has nearly the same proportions of isomers as the starting material.

The hemifumarate of the amine function is then prepared as follows: 11.45 g of the oil obtained are dissolved in 50 ml of ethanol, and 4.3 g of fumaric acid are added. The solution is heated to reflux for a quarter of an hour and then cooled. One volume of ethyl ether is added. The precipitate obtained is isolated. It consists of at least 90% of the isomer with the cis configuration in relation to the benzene nucleus. The filtrate is made alkaline by the addition of sodium carbonate. The ethanol is then evaporated under reduced pressure and the desired product is extracted with diethyl ether in the form of the amine. After dessication of the solution, the amine hydrochloride is prepared by the addition of anhydrous hydrochloric acid. The precipitate is filtered and dried. Purification is then carried out by preparing solutions of this hydrochloride in a solvent at 25° C., preferably ethanol, from which it is reprecipitated by the addition of diethyl ether. 1.5 g of the hydrochloride of the geometric trans isomer (in relation to the benzene nucleus) of 7-chloro-3,4-dihydro-1-benzoxepin-O-(diethylaminoethyl)-5-one oxime are obtained. This isomer melts at 144° C.

Examples 4 and 5 illustrate two other methods of preparing the products of example 2.

EXAMPLE 4

Preparation of 7-chloro-3,4-dihydro-1-benzoxepin-O-(diethylaminoethyl)-5-one oxime from 7-chloro-3,4-dihydro-1-benzoxepin-5-one and O-(diethylaminoethyl)-hydroxylamine 10.25 g of the dihydrochloride of O-(diethylaminoethyl)-hydroxylamine are added to a solution of 19.65 g of 7-chloro-3,4-dihydro-1-benzoxepin-5-one in 100 ml of absolute ethanol and the solution is heated at the reflux temperature of the solvent for 5 hours. After 1½ hours' of refluxing, a further 10.25 g of the dihydrochloride of O-(diethylaminoethyl)-hydroxylamine are introduced into the reaction mixture.

The solvent is then evaporated under reduced pressure. A dilute hydrochloric acid solution is poured over the residue and the aqueous phase obtained is washed with ether and then made alkaline by the addition of sodium carbonate.

The end product is then extracted from this phase with ether. The organic phase is dried over sodium sulphate and then over magnesium sulphate and the solvent is evaporated under reduced pressure. 13.9 g of oil are obtained.

The hydrochloride of the end product is prepared in ether by the action of gaseous hydrochloric acid. After recrystallisation from a mixture of isopropyl ether and 1,2-dichloroethane (60:40) in the presence of animal charcoal, 10.5 g of the desired hydrochloride of the product are obtained in the form of white crystals which melt at 115°–116° C.

The hemifumarate of the end product is prepared in ethanol by the addition of an equimolecular proportion of fumaric acid to the amine solution followed by precipitation by the addition of petroleum ether. After recrystallisation from a mixture of isopropanol and isopropyl ether (50:50), the pure hemifumarate melts at 98° C.

EXAMPLE 5

Preparation of 7-chloro-3,4-dihydro-benzoxepin-O-(diethylaminoethyl)-5-one oxime from 7-chloro-3,4-dihydro-1-benzoxepin-5-one oxime A mixture of 5.3 g of 7-chloro-3,4-dihydro-1-benzoxepin-5-one oxime, 4.3 g of the hydrochloride of (2-chloro)-ethyl diethylamine, 10.7 g of potassium carbonate and 50 ml of benzene is kept at the reflux temperature of the solvent for 15 hours. The mineral precipitate is then filtered, the benzene phase is washed with a normal aqueous soda solution and the end product is extracted with a normal aqueous solution of hydrochloric acid. After washing with ether, the aqueous phase is made alkaline by the addition of sodium carbonate and the end product is extracted with ether. After drying the solution and evaporation of the solvent, 7.8 g of yellow oil are obtained, from which 6.3 g of the hydrochloride of the desired basic oxime ether are prepared. Melting point of the hydrochloride: 115°–116° C.

EXAMPLE 6

7-chloro-3,4-dihydro-1-benzoxepin-O-(morpholinoethyl)-5-one oxime 11 g of this compound are obtained by the method described in example 1 from 7.6 g of 7-chloro-3,4-dihydro-1-benzoxepin-5-one oxime and 6 g of N-(2-chloroethyl)-morpholine.

The hydrochloride prepared in hydrochloric ether and recrystallised from ethyl acetate melts at 140° C.

EXAMPLE 7

7-chloro-3,4-dihydro-1-benzoxepin-O-(1-pyrrolidinylethyl)-5-one oxime 16.3 g of the dihydrochloride of 0-(1-pyrrolidinylethyl)hydroxylamine (Mp. = 150° C.) and a few drops of concentrated hydrochloric acid are added to 15.7 g of 7-chloro-3,4-dihydro-1-benzoxepin-5-one dissolved in 100 ml of 95% ethanol, and the reaction mixture is heated to the reflux temperature of the solvent for 6 hours.

The solvent is evaporated under reduced pressure. The residue is taken up with 1 N hydrochloric acid, unreacted ketone is extracted with ether, the aqueous phase is made alkaline by the addition of sodium carbonate and the amine required as end product is extracted with benzene.

The benzene solution is copiously washed with water and then dried over magnesium sulphate and the solvent is evaporated under reduced pressure.

The hydrochloride of the amine is prepared in hydrochloric ether and then recrystallised from isopropanol. It melts at 154°–155° C. The yield in relation to the ketone is 45%.

EXAMPLE 8

7-chloro-3,4-dihydro-1-benzoxepin-O-(dimethylaminopropyl)-5-one oxime

Applying the method of preparation described in example 1 and reacting 7.6 g of oxime and 4.9 g of (3-chloro)-propyl dimethylamine at stage (C), 7 g of crude end product are obtained in the form of an oil.

The hydrochloride prepared in hydrochloric ether melts at 166° C. after recrystallisation from bisopropanol.

EXAMPLE 9

7-methoxy-3,4-dihydro-1-benzoxepin-O-(dimethylaminoethyl)-5-one oxime

A—7-methoxy-3,4-dihydro-1-benzoxepin-5-one 40 ml of concentrated phosphoric acid (d=1.71) are added to 300 ml of anhydrous toluene. 70 g of phosphorous pentoxide are then added slowly with vigorous stirring. The mixture is kept on a boiling water bath for 2 hours. A tepid solution of 20 g of p-methoxy phenoxybutyric acid (Mp.=104° C.) in 1 liter of anhydrous toluene is then added to this temperature in the course of 2 hours. The mixture is kept on a boiling water bath for a further 3 hours and then cooled. The upper toluene phase is decanted and the lower phase is poured over 2 volumes of crushed ice. When the whole mixture has returned to room temperature, the organic products are extracted with ethyl acetate. After this phase has been washed with water and then with a sodium bicarbonate solution and neutralised, it is dried over magnesium sulphate and the solvent is evaporated under reduced pressure. 15.4 g of an oil are obtained. After distillation, it yields 12 g of 7-methoxy-3,4-dihydro-1-benzoxepin-5-one which has a boiling point of 110° C. at 0.02 mm. Hg.

B—7-methoxy-3,4-dihydro-1-benzoxepin-5-one oxime 6.95 g of hydroxylamine hydrochloride dissolved in 15 ml of water and 5.3 g of sodium carbonate are added to a solution of 19.2 g of 7-methoxy-3,4-dihydro-1-benzoxepin-5-one in 45 ml of ethanol. The mixture is left at room temperature for 24 hours with stirring. 100 ml of water are then added and the alcohol is evaporated. The aqueous solution is make alkaline by the addition of soda and unreacted benzoxepin is extracted with ether. The aqueous phase is neutralised and the desired oxime is extracted with ether. After drying of the organic solution and evaporation of the solvent under reduced pressure, a white solid is obtained which, when recrystallised from cyclohexane yields 17 g of the desired pure product which has a melting point of 103° to 104° C.

C—7-methoxy-3,4-dihydro-1-benzoxepin-O-(dimethylaminoethyl)-5-one oxime 5.84 g of oxime prepared as indicated above are added to 30 ml of a sodium ethylate solution prepared from 0.8 g of sodium, and the mixture is heated on a boiling water bath for 1 hour. 30 ml of anhydrous dimethylformamide are then added and the alcohol is evaporated under reduced pressure.

3.2 g of (2-chloro)-ethyl dimethylamine are added and the reaction mixture is kept on a boiling water bath for 1 hour.

The solvent is evaporated under reduced pressure. The residue is taken up in an aqueous 10% hydrochloric acid solution, and this phase is washed once with ether and made alkaline by the addition of 10% soda.

The end product is extracted with methylene chloride, the organic phase is dried and the solvent is evaporated under reduced pressure. The oil obtained is distilled. Boiling point: 160° C. at 0.5 mm.Hg.

4.1 g of amine are obtained as end product. The hydrochloride prepared in hydrochloride ether and recrystallised from isopropanol melts at 178° C.

EXAMPLE 10

7-methoxy-3,4-dihydro-1-benzoxepin-O-(diethylaminoethyl)-5-one oxime

Applying the method of preparation described in example 9 and reacting 7.25 g of oxime and 6.8 g of (2-chloro)-ethyl diethylamine at stage (C), 7 g of crude amine are obtained as end product.

The hydrochloride prepared in hydrochloric ether melts at 108° C. after recrystallisation from ethyl acetate.

EXAMPLE 11

7-methoxy-3,4-dihydro-1-benzoxepin-O-dimethylaminopropyl)-5-one oxime

Applying the method of preparation described in example 9 and reacting 5.85 g of oxime and 4 g of (3-chloro)-propyl-dimethylamine at stage (C), 6.2 g of the amine are obtained in the form of a yellow oil.

The hemioxalate of the amine is prepared in ethanol by reacting the amine and acid in equimolecular proportions. After recrystallisation from ethanol, the pure hemioxalate melts at 130° C.

EXAMPLE 12

7-bromo-3,4-dihydro-1-benzoxepin-O-(diethylaminoethyl)-5-one oxime

A—7-bromo-3,4-dihydro-1-benzoxepin-5-one This heterocyclic ketone is prepared by the method described in example 1(A) from p-bromophenoxybutyric acid (Mp.=132° C.) with a 40% yield. Its boiling point is 105° C. at 0.06 mm.Hg.

B—7-bromo-3,4-dihydro-1-benzoxepin-O-(diethylaminoethyl)-5-one oxime

The amine is prepared by reacting the benzoxepinone previously obtained with the hydrochloride of O-(diethylaminoethyl)hydroxylamine by the method described in example 4. 4.5 g of end product in the form of an oil are obtained from 7 g of 7-bromo-3,4-dihydro-1-benzoxepin-5-one.

The hydrochloride of this amine is prepared in ether by the action of gaseous hydrochloric acid and purified by dissolving in ethanol and reprecipitating by the addition of diethyl ether. It melts at 138° C.

The yield of hydrochloride from the ketone is 50%.

Toxicological and pharmacological tests carried out on the products of the invention demonstrated the originality of their activity as compared with known products. The tests were carried out on acid addition salts of the amines of the general formula.

The acute toxicity was determined in male Swiss C.D. mice weighing an average of 20 grammes, after oral administration (P.O) and intravenous administration (I.V.).

The relaxant activity at the level of the smooth intestinal muscle fibre was demonstrated in vitro on isolated organs and in vivo on the anaesthetised dog, employing the following techniques:

For tests on the isolated organ: An organ fragment of rat duodenum or guinea pig ileum is kept alive in 50 ml of oxygenated and thermostatically controlled (37° C.) Tyrode solution. The activity of the compounds is tested on the spontaneous movements of the organ and the contractions produced by the addition of solution of barium chloride or acetyl choline to the bath. The movements were recorded on a DMP 4A Roucaire physiograph.

For the in vivo tests: a balloon is introduced into the chloralosed animal at the level of the terminal part of the duodenum and the intestinal movements are recorded on a Beckman polygraph with the acid of Statham PM 97 gauge.

The results relating to the acute toxicity and relaxant activity in vitro are shown in Table I.

The in vivo tests showed that the products of the invention and in particular those of examples 1, 2, 7, 8 and 12 administered at a dose of 2 mg/kg intravenously had an effect which was comparable with or even superior to that of atropine administered in a dose of 50 mg/kg as regards the reduction in muscle tone and intestinal peristalsis. In contrast, to atropine, however, this relaxant activity exists apart from any anticholinergic and vagolytic activity.

The pharmaceutical compositions containing, as an active ingredient, at least one product according to the invention may be presented, for example, in the form of tablets or preparations for injection.

The tablets may contain about 75 mg of active ingredient and known excipients such as microcrystalline cellulose, carboxymethyl starch, talcum and magnesium stearate.

The ampoules for injection may contain about 25 mg of active ingredient and a sufficient quantity of glycine to make the product isotonic.

TABLE 1

| Compound of example | Toxicity in mice LD$_{50}$ (mg/kg) P.O. | Toxicity in mice LD$_{50}$ (mg/kg) I.V | ISOLATED ORGANS: Minimum active dose concentration in mcg/ml Decontraction (rat duodenum) | ISOLATED ORGANS: Minimum active dose concentration in mcg/ml Anti-Acetyl-Choline (guinea pig ileum) |
|---|---|---|---|---|
| 1 (hydrochloride) | 150 | 32 | 0.06 | 5.5 |
| 2 (hydrochloride) | 420 | 37 | 0.1 | 1 |
| 6 (hydrochloride) | >1000 | 120 | 0.15 | 5.5 |
| 7 (hydrochloride) | 450 | 35 | 1.5 | 1.3 |
| 8 (hydrochloride) | 500 | 60 | 0.12 | 3.5 |
| 9 (hydrochloride) | 500 | 35 | 0.12 | 1.5 |
| 10 (hydrochloride) | 450 | 45 | 0.5 | 0.5 |
| 11 (hemioxalate) | >1000 | — | 0.3 | 2.0 |
| 12 (hydrochloride) | 250 | 40 | 0.1 | 1 |
| ATROPINE (sulphate) | 600 | 90 | inactive | 0.006 |

We claim:

1. A therapeutic composition particularly for treating intestinal disorders comprising a therapeutically effective amount of at least one isomer of the oximino group of the compound having the formula

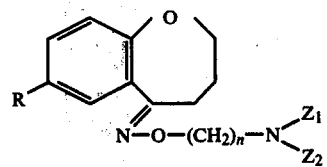

in which:
R is selected from the group consisting of halogen atoms and lower alkoxy groups;
n is an integer 2 or 3, and
$Z_1$ and $Z_2$ are the same or different lower alkyl groups, or
$NZ_1Z_2$ represents a saturated heterocyclic group which may have a second heteroatom selected from the group consisting of N and O,
and the addition salts of the amino group with pharmaceutically acceptable acids,
with a physiological acceptable excipient.

2. A therapeutic composition as claimed in claim 1, wherein said compound is 7-chloro-3,4 dihydro-1-benzoxepin-0-(diethylaminoethyl)-5-one oxime, and its acid addition salts.

3. A method of treating colopathics, particularly diarrhea and constipation, which comprises administering to a human an effective amount, in unit dosage form of the compound of claim 1.

* * * * *